United States Patent
Saint Martin

(12) 
(10) Patent No.: US 6,730,093 B2
(45) Date of Patent: May 4, 2004

(54) ANCHORING MEMBER WITH PACKER

(75) Inventor: Pierre Henri Saint Martin, Mérignac (FR)

(73) Assignee: Stryker Spine (FR)

(*) Notice: Subject to any disclaimer, the term of this patent is extended or adjusted under 35 U.S.C. 154(b) by 0 days.

(21) Appl. No.: 10/096,989

(22) Filed: Mar. 13, 2002

(65) Prior Publication Data

US 2002/0133158 A1 Sep. 19, 2002

(30) Foreign Application Priority Data

Mar. 15, 2001 (FR) .............................. 01 03514

(51) Int. Cl.[7] .......................... A61B 17/56; F16B 43/00
(52) U.S. Cl. ......................................... 606/72; 411/533
(58) Field of Search .............................. 606/60, 61, 71, 606/72, 73; 411/533, 368, 369, 542

(56) References Cited

U.S. PATENT DOCUMENTS

| | | | | |
|---|---|---|---|---|
| 1,352,285 A | * | 9/1920 | Landgraf | 29/890.051 |
| 1,409,157 A | * | 3/1922 | Dodds | 411/379 |
| 1,616,232 A | | 2/1927 | Roberts et al. | |
| 2,511,051 A | | 6/1950 | Dzus | |
| 4,615,655 A | * | 10/1986 | Dixon | 411/339 |
| 5,056,208 A | * | 10/1991 | Stafford | 29/515 |
| 5,269,784 A | | 12/1993 | Mast | |
| 5,542,777 A | | 8/1996 | Johnson | |
| 5,607,426 A | | 3/1997 | Ralph et al. | |
| 5,690,632 A | | 11/1997 | Schwartz et al. | |
| 5,738,685 A | | 4/1998 | Halm et al. | |
| 5,797,912 A | * | 8/1998 | Runciman et al. | 606/69 |
| 5,899,906 A | | 5/1999 | Schenk | |
| 5,975,821 A | * | 11/1999 | Kue | 411/533 |
| 5,976,141 A | | 11/1999 | Haag et al. | |
| 6,010,505 A | | 1/2000 | Asche et al. | |
| 6,063,090 A | | 5/2000 | Schlapfer | |
| 6,241,731 B1 | * | 6/2001 | Fiz | 606/65 |
| 6,302,887 B1 | | 10/2001 | Spranza et al. | |
| 6,331,179 B1 | * | 12/2001 | Freid et al. | 606/61 |
| 2002/0055743 A1 | * | 5/2002 | Seemann | 606/73 |

FOREIGN PATENT DOCUMENTS

| | | |
|---|---|---|
| AT | 386 118 | 7/1988 |
| DE | 39 42 326 | 6/1991 |
| DE | 295 21 456 | 6/1997 |
| DE | 296 15 482 | 2/1998 |
| EP | 0 997 107 A2 | 5/2000 |
| FR | 2 555 645 A1 | 5/1999 |
| FR | 2 642 643 | 8/1990 |
| FR | 2 642 643 A2 | 8/1990 |
| FR | 2 659 546 A1 | 9/1991 |
| FR | 2 659 546 | 9/1991 |
| GB | 2 324 964 | 11/1998 |

OTHER PUBLICATIONS

French Preliminary Search Report dated Oct. 8, 2001.
EP—0 997 107A3—European Search Report dated Jun. 7, 2001.

* cited by examiner

*Primary Examiner*—Pedro Philogene
*Assistant Examiner*—David Bonderer
(74) *Attorney, Agent, or Firm*—Lerner, David, Littenberg, Krumholz & Mentlik, LLP

(57) ABSTRACT

An anchoring member and packer for use in spinal osteosynthesis systems. The anchoring member can accept a connecting element such as a spinal rod, and is adapted for insertion into bone. The packer provides stability to the anchoring member particularly when the anchoring member is not fully engaged to bone. The anchoring member has a head, anchoring means for engagement to bone, and retaining means for retaining the packer against the head. The packer has a through-orifice for receiving the anchoring member and complimentary retaining means for engagement to the head of the anchoring member.

21 Claims, 3 Drawing Sheets

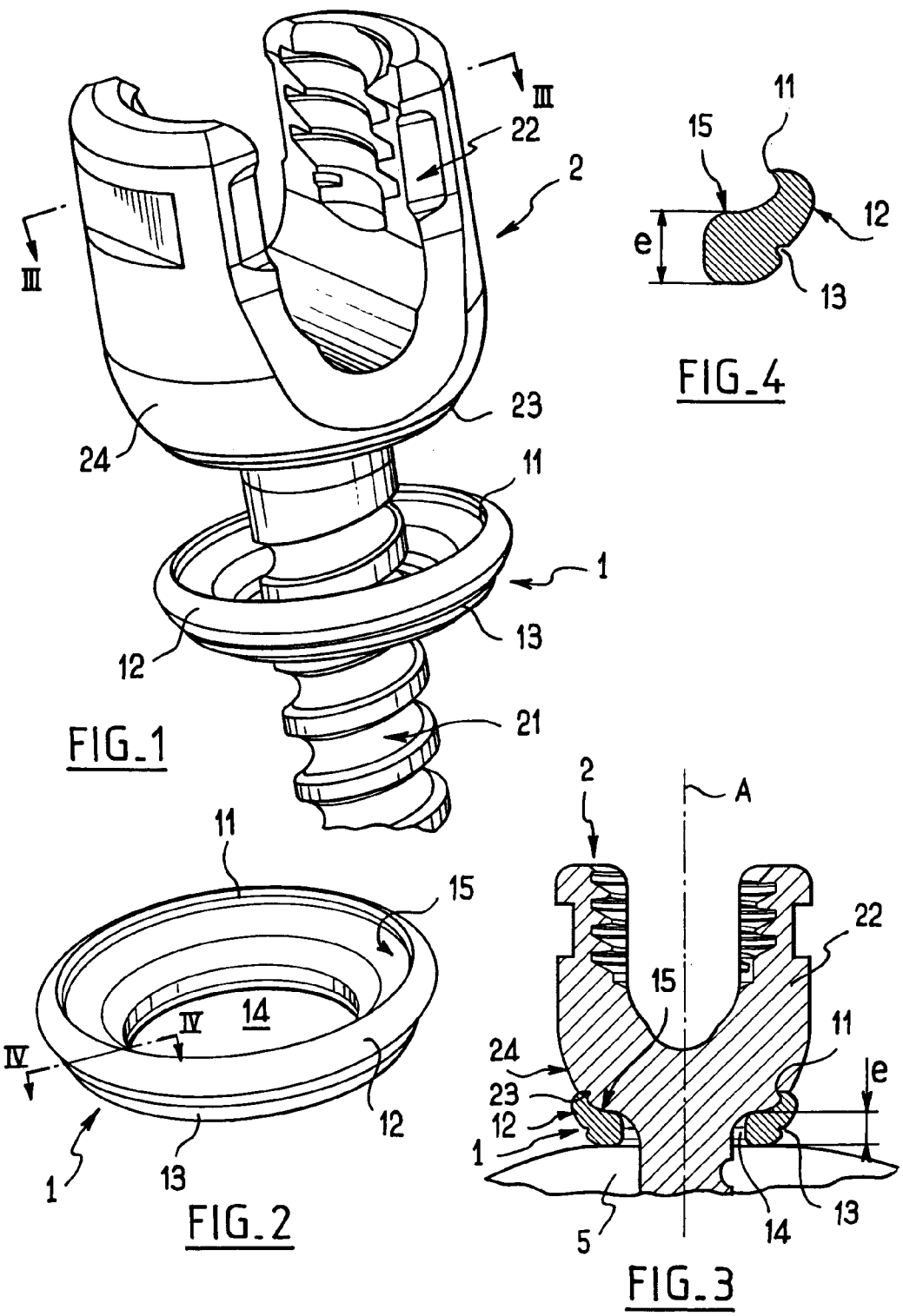

ANCHORING MEMBER WITH PACKER

This application claims priority benefits under Title 35i United States Code, § 119 (a)–(d) of a foreign application filed in France. The application number is 01 03514 and was filed on Mar. 15, 2001.

BACKGROUND OF THE INVENTION

The invention relates to spinal osteosynthesis systems.

Spinal osteosynthesis systems generally comprise bone screws, such as pedicle screws. Sometimes, during the surgical operation, one or more screws are not screwed fully home, that is, the cortical thread is not fully engaged in the bone of the vertebra. This occurs for various reasons. One reason may be because the screw is too long and because, if it were screwed fully home, the distal end of the thread would re-emerge from the bone on the opposite side to the side via which the screw entered, digging into the tissues located on that side. Another reason may be an anatomical defect leading to the fact that, if the screw were screwed fully home, it would be screwed in further than the other screws of the osteosynthesis system. This leading to exaggerated and difficult-to-achieve bowing of the connecting member. To avoid this, the surgeon does not screw the screw fully into the bone, leaving the proximal part of the cortical thread disengaged from the bone. However, this has the disadvantage of making the screw unstable in the bone because this screw is not tight, as well as the disadvantage of leaving bone threads outside the bone in which the member is anchored, which leads to damage to the surrounding tissue because of the presence of the sharp corners of the screw thread.

One object of the invention is to provide a system which makes it possible to better stabilize an anchoring member while at the same time better isolating the non-engaged anchoring part from the adjacent environment.

SUMMARY OF THE INVENTION

This and other objects are achieved by the present invention, which is a spinal osteosynthesis assembly comprising an anchoring member having a head with a bone engaging portion, and at least one packer that contacts bone, and is able to be coupled to the anchoring member.

Advantageously, the part of the bone engaging portion of the anchoring member which is not engaged in the bone finds itself at least partially surrounded by the packer which isolates it from the adjacent environment. Additionally, since the packer contacts the bone, this provides better stability. In consequence, the anchoring member is stabilized and the non-engaged part of the bone engaging portion can no longer damage the tissue surrounding the anchoring member.

Advantageously, the packer has a slot such that the packer forms a non-closed annulus.

Advantageously, the packer is elastically deformable to facilitate movement of the bone engaging portion through the slot. Thus, the packer can be fitted over the anchoring member when the latter is already anchored in the bone.

Advantageously, the packer is in the shape of an annulus and the packer has a lip, while the anchoring member has a groove such that engagement of the lip with the groove facilitates coupling the packer to the anchoring member. Thus, the packer may be clipped onto the anchoring member in a simple movement. Also advantageously, the lip may be discontinuous.

Advantageously, in addition to the lip, the packer has a recess and is stackable to another packer via engagement of the lip of one packer to the recess of another packer.

There is also provided, according to the invention, a surgical method exhibiting the steps of fitting the packer onto the anchoring member, and inserting the anchoring member into the bone.

Advantageously, the method exhibits the steps of fitting the anchoring member into the bone, and then fitting the packer to the anchoring member.

Advantageously, the method exhibits an additional step of anchoring the anchoring member to the extent that the packer contacts the bone.

Other features and advantages of the invention will become apparent from reading the description herein below of one preferred embodiment and of some alternative forms.

BRIEF DESCRIPTION OF THE DRAWINGS

FIG. 1 is a three-dimensional view of a first embodiment of the invention.

FIG. 2 is a three-dimensional view of the packer of the first embodiment.

FIG. 3 is a view along section III—III of FIG. 1.

FIG. 4 is a view along section IV—IV of FIG. 2.

DETAILED DESCRIPTION OF THE INVENTION

Figure 5:
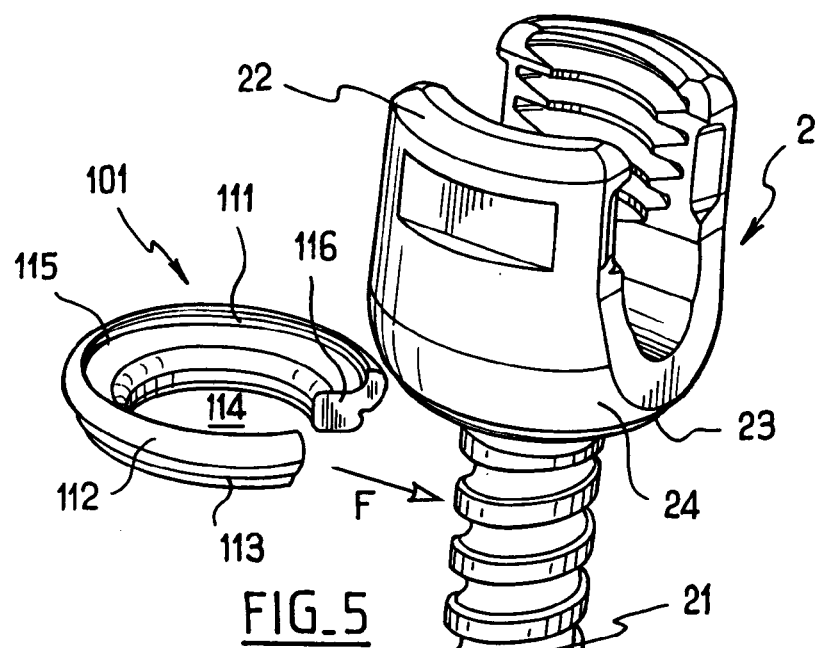
FIG. 5 is a three-dimensional view of a second embodiment of the invention.

For all the embodiments which are going to be described, just one anchoring member 2 is depicted, the remainder of the osteosynthesis system not being depicted.

In a way which is common to all the embodiments, an osteosynthesis system comprises a number of anchoring members 2, in this instance monoaxial bone screws, at least one connecting element (not depicted), in this instance connecting rods of circular cross section, and locking means (not depicted) for locking the connecting elements to the anchoring members, in this instance bolts. Each anchoring member 2, of the osteosynthesis system consists of two main parts. One is a lower part 21, in this instance of cylindrical shape with a circular cross section having a bone thread, that is able to engage and anchor in the bone. Another is an upper part 22 of the anchoring member, which is known as the "screw head". The upper part 22 comprises two parallel branches extending opposite each other and delimiting a U-shaped opening capable of accommodating the connecting element. The interior faces facing each other of the branches forming the U have a screw thread capable of collaborating with a complementary screw thread belonging to the locking means. Such anchoring members are described in patents FR 2,642,643 and FR 2,659,546 to which reference will be made for further details. The upper part 22 and the lower part 21 of each anchoring member 2 are connected to one another forming a surface 24 which has a circular cut 23 of roughly V-shaped cross section extending around the entire circumference of the surface 24.

With reference to FIGS. 1 to 4, a first embodiment of the invention will be described. The packer 1 has an annular shape and exhibits a lateral external surface 12 and a lateral internal surface 15, the lateral internal surface 15 delimiting a central through-opening 14. The upper end of the internal surface 15 comprises a lip 12 on its entire circumference. The external lateral surface 12 comprises, in its lower part, a circular cut 13 of roughly V-shaped cross section running around the entire circumference of the annulus. The internal lateral surface 15 more or less complements the part of the face 24 of the anchoring member 2 that lies between the cut 23 and the lower part 21 of the anchoring member 2. Furthermore, the part of the external lateral surface 12 that lies below the circular cut 13 of the packer 1 more or less complements the upper part of the internal lateral surface 15. The packer 1 has a working thickness e measures parallel to an axis A perpendicular to the overall plane of the packer.

The use of the first embodiment of the invention will now be described. The surgeon, before fitting the anchoring member into the bone at the desired location, fits the anchoring member 2 and the packer 1 together. To do that, part 21 exhibiting the bone thread is slipped through the orifice 14 of the packer 1 until the lip 11 comes into contact with the surface 24 of the anchoring member. At that moment, the lip 11 lies near the cut 23. The surgeon applies additional force to the packer so that the lip 11 engages in the cut 23. To obtain that result, the surgeon has made use of the elasticity of the material of which the packer 1 is made. This material is biocompatible, so that it can be tolerated by the human body. This may be stainless steel, such as 316L, titanium, or alternatively a titanium alloy such as TA6V4, or alternatively a polymer such as PEEK (polyetheretherketone). Once this assembly has been achieved, the surgeon fits the anchoring member into the patient in such a way that, for preference, the packer contacts the bone 5, as illustrated in FIG. 3. The surgeon then continues the surgical operation.

Figures 6, 7:
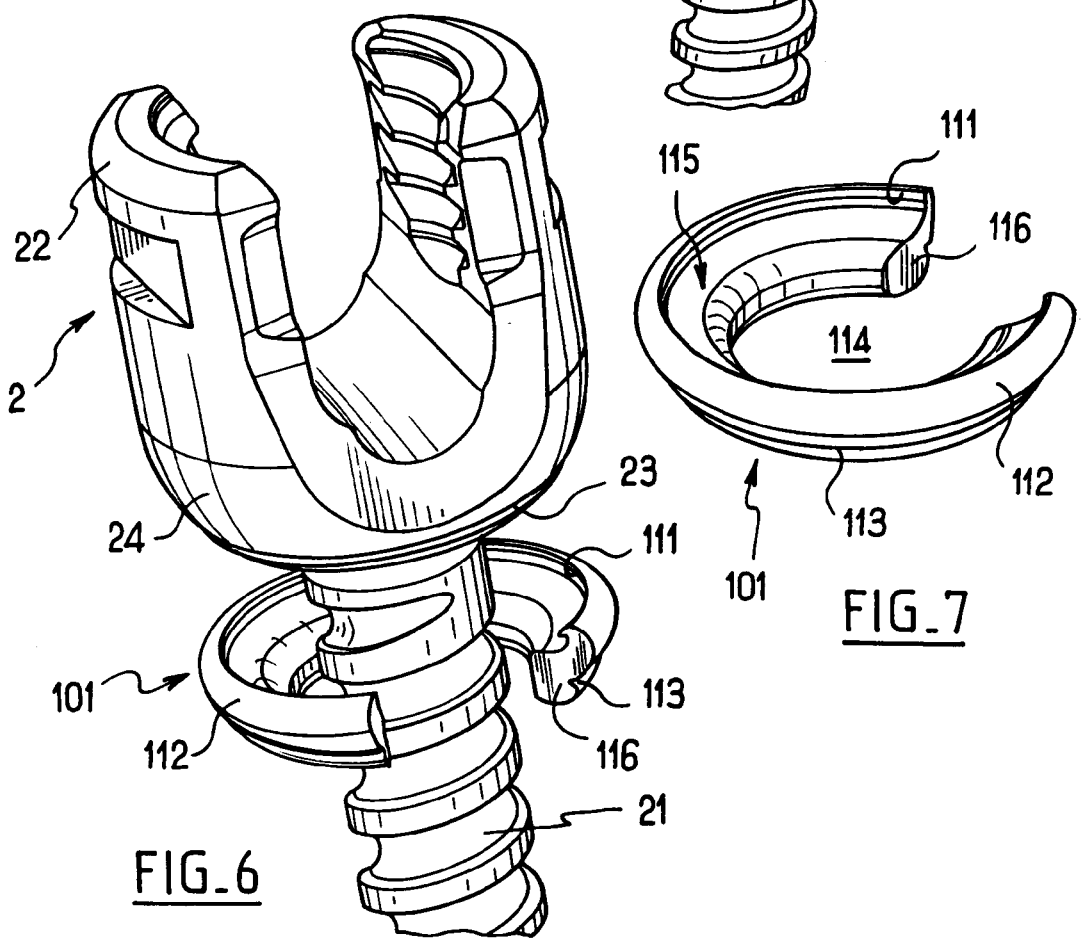
FIG. 6 is a three-dimensional view of the second embodiment during fitting.
FIG. 7 is a three-dimensional view of the packer of the second embodiment.

With reference to FIGS. 5 to 7, a second embodiment of the invention will be described. The packer 101 is very similar to the packer 1 of the previous embodiment. This packer is formed of an annulus of a cross section identical to the cross section of the annulus that forms the packer 1. The surface 115 is identical to the surface 15. Likewise, the surface 112 is identical to the surface 12. The upper end of the surface 115 has a lip 111 identical to the lip 11. Likewise, the surface 112 has a cut 113 identical to the cut 13. The lateral internal surface 115 delimits an orifice 114. The difference lies in the fact that the packer 101 has a slot 116, thus forming a non-closed annulus. This slot 116 has an opening, the width of which is roughly equivalent to the diameter of the lower part 21 of the anchoring member 2.

Figure 8:
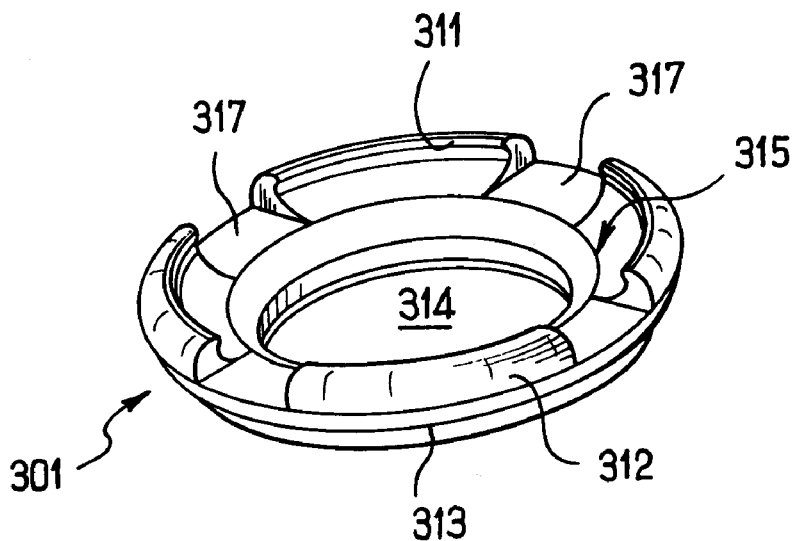
FIG. 8 is a three-dimensional view of a packer of a third embodiment of the invention.

In use, the surgeon can fit the packer 101 over the anchoring member 2 before fitting the anchoring member 2 into the patient, or alternatively he may install the packer 101 after he has positioned the anchoring member 2 in the patient. In the former instance, fitting together is done in the same way as in the previous embodiment of the invention. In the latter instance, the surgeon has fitted the anchoring member 2 while an anchoring portion of the lower part 21 of the anchoring member 2 is not engaged in the bone and projects out from the bone. To protect the surrounding tissues and organs on the one hand, and on the other hand to better stabilize the anchoring member, the surgeon will insert a packer between the head 22 of the anchoring member 2 and the surface of the bone. To do that, the surgeon clips the packer 101 under the head 22 of the anchoring member 2 as follows. As indicated in FIG. 5 by the arrow F, the part 21 is inserted into the orifice 114 and through slot 116. As the part 21 is passing through the slot 116, the slot 116 opens up slightly because of the elasticity of the material of the packer, to allow the part 21 to pass. Once this part 21 is in the orifice 114, the slot 116 returns to its previous configuration, closing up on itself through the elasticity of the material of which the packer 101 is made. The surgeon then has merely to exert a force similar to the force that he would have exerted in the previous embodiment in order to insert the lip 111 of the packer 101 into the cut 23 of the anchoring member 2. The packer 101 is fitted onto the anchoring member 2 as illustrated in FIG. 8. Next, the surgeon continues his surgical operation in the normal way.

With reference to FIG. 8, a third embodiment of the invention will be described. The packer 301 differs from the packer 1 in that grooves 317 distributed uniformly around the entire circumference of an upper part of the packer 301 split the lip 311 into roughly identical angular sectors. In this instance, there are four grooves 317. Thus, on fitting, elastic deformation of the packer 301 is easier when inserting the lip 311 into the cut 23 of the anchoring member 2. In consequence, the surgeon supplies a force which is weaker than the force supplied to the packer 1 of the first embodiment for clipping the packer 301 onto the anchoring member 2.

The use of the packer 301 is identical to the use of the packer 1 in the first embodiment.

Figure 9:
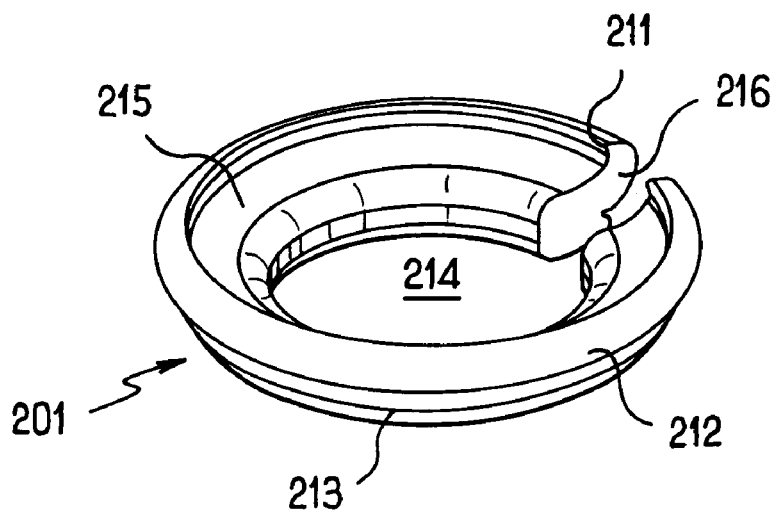
FIG. 9 is a three-dimensional view of a fourth embodiment of the packer of the invention.

With reference to FIG. 9, according to a fourth embodiment of the invention, the packer 201 is identical to the packer 101 except that the opening of the slot 216 is far smaller. This slot 216 does not allow the part 21 of the anchoring member 2 to be introduced sideways into the orifice 214. This packer 201 is fitted in the same way as the packer 1 described earlier. Just like with the third embodiment of the invention, the deformation of the ring 201 is made easier by the presence of the slot 216 during clipping to introduce the lip 211 into the cut 23. In consequence, the surgeon supplies a force which is weaker than the force he supplies for the packer 1 of the first embodiment for fitting the packer 201 onto the anchoring member 2.

For all the embodiments, as the packers comprise on their exterior surface a cut identical to the cut made on the anchoring member, these packers can be stacked up as the surgeon sees fit, the lip of the packer below clipping into the cut of the packer above. It is thus possible for two or more packers to be slipped over and fitted onto the anchoring member.

Of course it is possible to make numerous modifications to the present invention without in any way departing from its scope. For example, the lips and the cut could be replaced by complementing conical surfaces delimiting what are known as "Morse tapers". The lips may also be replaced by a screw thread while the cut may be replaced by a groove surmounting a screw thread that complements the thread. Thus, the packer will be fixed to the screw thread until the thread enters the groove where it will be held captive.

Still further, the lips may be replaced by a number of studs projecting toward the central orifice of the packer and distributed uniformly around the circumference of the packer, while the cut may be replaced by housings, of which there would be the same number as there are studs, which housings could accommodate and retain the studs.

The anchoring member could be any type of bone screw, of the polyaxial or monoaxial type. The connection between the anchoring member and the packer could lie at the head, or alternatively at the anchoring part of the member.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A spinal osteosynthesis assembly comprising:

an anchoring member having a head and a bone engaging portion; and a stackable packer comprising a through-orifice capable of receiving the anchoring member;

wherein the stackable packer is positioned between the head of the anchoring member and the bone, the stackable packer is able to contact bone, and is able to be coupled to the head of the anchoring member wherein the stackable packer further comprises a lip and the anchoring member further comprises a groove, such that the engagement of the lip with the groove facilitates coupling the stackable packer to the anchoring member.

2. The spinal osteosynthesis assembly of claim 1, wherein a slot is arranged on the stackable packer such that the packer forms a non-closed annulus.

3. The spinal osteosynthesis assembly of claim 2, wherein the stackable packer is elastically deformable to facilitate movement of the bone engaging portion through the slot.

4. The spinal osteosynthesis assembly of claim 1, wherein the stackable packer further comprises a recess having a shape complimentary to the lip, such that the recess facilitates stacking the stackable packer to another stackable packer.

5. The spinal osteosynthesis assembly of claim 4, wherein the stackable packer is stackable to other stackable packers via interengagement of respective lips to recesses.

6. The spinal osteosynthesis assembly of claim 1, wherein the lip is discontinuous.

7. The spinal osteosynthesis assembly of claim 1, wherein at least two stackable packers are stacked together.

8. The spinal osteosynthesis assembly of claim 7, wherein at least two stackable packers comprise a first stackable packer having a first lip and first recess, and a second stackable packer having a second lip and second recess, and wherein the first stackable packer is coupled to the anchoring member via attachment of the first lip to the groove of the anchoring member and the second stackable packer is coupled to the first stackable packer via attachment of the second lip to the first recess.

9. The spinal osteosynthesis assembly of claim 8, wherein the second stackable packer contacts the bone.

10. The spinal osteosynthesis assembly of claim 1, wherein a plurality of stackable packers form a stack, the stack is positioned between the head of the anchoring member and the bone, one of the plurality of stackable packers contacts the bone, and another of the plurality of stackable packers is coupled to the head of the anchoring member via the engagement of the lip with the groove.

11. A spinal osteosynthesis assembly comprising:

an anchoring member having a head, a bone engaging portion, and a groove; and a packer comprising an annulus, a through-orifice capable of receiving the anchoring member, and a lip;

wherein the packer is positioned between the head of the anchoring member and the bone, the packer is able to contact bone, and is able to be coupled to the anchoring member via elastically deformable engagement of the lip with the groove.

12. The spinal osteosynthesis assembly of claim 11, wherein a slot is arranged on the packer such that the packer forms a non-closed annulus.

13. The spinal osteosynthesis assembly of claim 11, wherein the packer is elastically deformable to facilitate movement of the bone engaging portion through the slot.

14. The spinal osteosynthesis assembly of claim 11 wherein the lip is discontinuous.

15. The spinal osteosynthesis assembly of claim 11, wherein the packer is stackable to other packers.

16. The spinal osteosynthesis assembly of claim 11, wherein the packer further comprises a recess.

17. The spinal osteosynthesis assembly of claim 16, wherein the packer is stackable to other packers via interengagement of respective lips to recesses.

18. The spinal osteosynthesis assembly of claim 11, wherein at least two packers are stacked together.

19. The spinal osteosynthesis assembly of claim 18, wherein the at least two packers comprise a first packer having a first lip and a first recess, and a second packer having a second lip and a second recess, and wherein the first packer is coupled to the anchoring member via attachment of the first lip to the groove of the anchoring member and the second packer is coupled to the first packer via attachment of the second lip to the first recess.

20. The spinal osteosynthesis assembly of claim 19, wherein the second packer contacts the bone.

21. The spinal osteosynthesis assembly of claim 11, wherein a plurality of packers form a stack, the stack is positioned between the head of the anchoring member and the bone, one of the plurality of packers contacts the bone, and another of the plurality of packers is coupled to the head of the anchoring member via the engagement of the lip with the groove.

* * * * *